US012005084B2

(12) United States Patent
Flower

(10) Patent No.: US 12,005,084 B2
(45) Date of Patent: Jun. 11, 2024

(54) COMPOSITION DERIVED FROM MAMMALIAN UMBILICAL CORD AND WHARTONS JELLY FOR USE IN THERAPEUTIC AND REGENERATIVE APPLICATIONS

(71) Applicant: Equi-Stem Biotechnologies LLC, West Bloomfield, MI (US)

(72) Inventor: Todd Flower, West Bloomfield, MI (US)

(73) Assignee: Equi-Stem Biotechnologies LLC, West Bloomfield, MI (US)

(*) Notice: Subject to any disclaimer, the term of this patent is extended or adjusted under 35 U.S.C. 154(b) by 774 days.

(21) Appl. No.: 16/731,911

(22) Filed: Dec. 31, 2019

(65) Prior Publication Data
US 2020/0129563 A1  Apr. 30, 2020

Related U.S. Application Data

(63) Continuation-in-part of application No. 15/660,921, filed on Jul. 26, 2017, now abandoned.
(Continued)

(51) Int. Cl.
*A61K 35/51*   (2015.01)
*A61K 9/00*    (2006.01)
(Continued)

(52) U.S. Cl.
CPC ............ *A61K 35/51* (2013.01); *A61K 9/0014* (2013.01); *A61K 35/28* (2013.01); *A61K 35/44* (2013.01); *C12N 5/0605* (2013.01)

(58) Field of Classification Search
CPC ..... A61K 35/51; A61K 9/0014; C12N 5/0605
See application file for complete search history.

(56) References Cited

U.S. PATENT DOCUMENTS

2012/0189583 A1* 7/2012 Liu .................. A61P 37/08
424/93.7
2013/0344163 A1* 12/2013 Tseng ............... A61K 35/51
424/583
2014/0295554 A1* 10/2014 Kim .................. C12N 5/0018
435/408

FOREIGN PATENT DOCUMENTS

KR         101063299      * 9/2011

OTHER PUBLICATIONS

Bai "Bioactive molecules derived from umbilical cord mesenchymal stem cells" Acta Histochemica 118 (2016): 761-769 (Year: 2016).*
(Continued)

*Primary Examiner* — Marcia S Noble
*Assistant Examiner* — Lauren K Van Buren
(74) *Attorney, Agent, or Firm* — Mark Terry

(57) ABSTRACT

A method of preparation of a solution used for therapeutic and regenerative applications having a concentration of at least about 0.05 microgram of total protein extract is disclosed. The method includes collecting an umbilical cord, incubating the umbilical cord in a solution containing antibiotics for sterilization, washing the umbilical cord in a buffered salt solution, homogenizing the umbilical cord in the buffered salt solution so as to produce an aqueous solution, applying an ultrasonic processer to the aqueous solution to sonicate and disrupt umbilical cord tissue, placing the aqueous solution into a centrifuge to separate the aqueous solution into a soluble component and a non-soluble component, filtrating and discarding the non-soluble component of the aqueous solution from the centrifuge through a 0.2 micron filter, and measuring protein concentration of the soluble component to insure at least about 0.05 microgram of total protein extract.

13 Claims, 13 Drawing Sheets

Related U.S. Application Data

(60) Provisional application No. 62/366,623, filed on Jul. 26, 2016.

(51) Int. Cl.
*A61K 35/28* (2015.01)
*A61K 35/44* (2015.01)
*C12N 5/073* (2010.01)

(56) References Cited

OTHER PUBLICATIONS

Weiss "Human Umbilical Cord Matrix Stem Cells: Preliminary Characterization and Effect of Transplantation in a Rodent Model of Parkinson's Disease" Stem Cells, 2006, 24: 781-792. (Year: 2006).*

* cited by examiner

05/09/2016 Wound Size 12cm X 4.5cm X 1.25cm
05/12/2016 Wound Size 12cm X 4.5cm X 1cm
05/16/2016 Wound Size 10cm X 4cm X 0.75cm
05/22/2016 Wound Size 7cm X 3.75cm X 0.5cm 06/15/2016
Wound Size
1 cm X 0.4 cm 06/13/2016
Wound Size
1 cm X 0.5 cm

FIG. 9B — Healed wound
FIG. 9A — Original wound

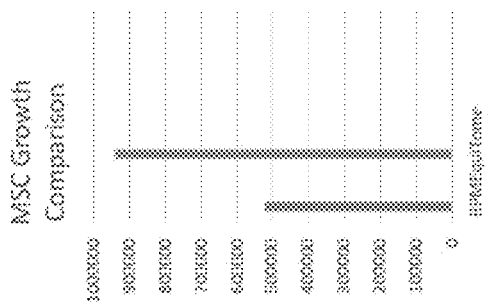
FIG. 13E
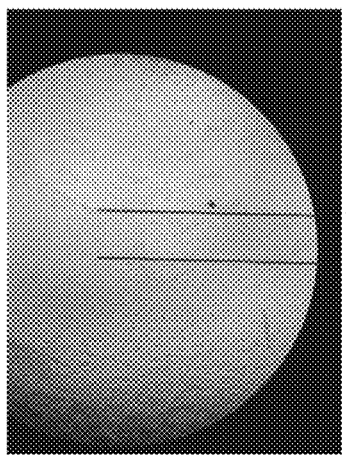
FIG. 13B
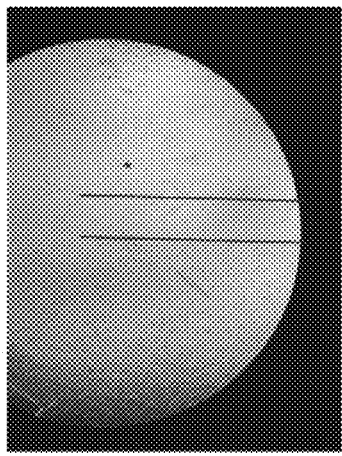
FIG. 13A
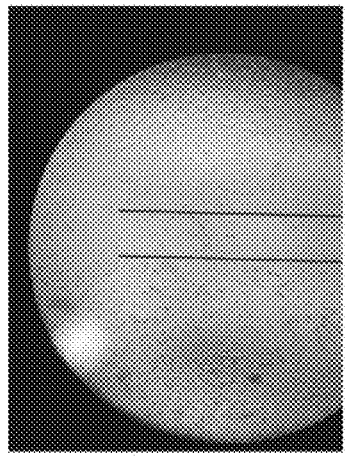
FIG. 13D
FIG. 13C

COMPOSITION DERIVED FROM MAMMALIAN UMBILICAL CORD AND WHARTONS JELLY FOR USE IN THERAPEUTIC AND REGENERATIVE APPLICATIONS

CROSS-REFERENCE TO RELATED APPLICATIONS

This application is a continuation-in-part of U.S. Non-Provisional patent application Ser. No. 15/660,921, filed Jul. 26, 2017, which claims the benefit of U.S. Provisional Application No. 62/366,623, filed Jul. 26, 2016. The subject matter all of which is incorporated herein by reference.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

TECHNICAL FIELD

The disclosed subject matter relates generally to the field of medicine and wellness, and, more specifically, relates to compositions with therapeutic and regenerative properties useful for the treatment of inflammation, wound healing, muscle healing, regeneration, articular pain, neurologic disorders and arthritis.

BACKGROUND

Umbilical cord tissue and Wharton's jelly is a tissue that surrounds the umbilical cord vessels. This tissue contains high amounts of extracellular matrix (ECM) components, mainly hyaluronic acid, collagen, and several sulphated proteoglycans and naïve cells that are referred to a Mesenchymal Stem Cells (MSCs). In addition, numerous growth factors and cytokines have been found to associate with extracellular matrix proteins. These growth factors and cytokines can control cell proliferation, inflammation, wound healing and remodeling, burns, anti-fibrotic (anti-scarring activity) and the synthesis and remodeling of the extracellular matrix. The claimed subject matter describes the extraction of these factors from umbilical cord tissue and their human and vet applications to treat a variety of conditions in both humans and animals.

Wharton's jelly, named after the person who first described it in his publication Adenographia, "The Description of the Glands of the Entire Body" published in 1656, is a gelatinous tissue which surrounds the umbilical cord vessels within the umbilical cord that contains myo-fibroblast-like stromal cells. See FIG. 1 for a cross sectional view of an umbilical cord. The extracellular matrix of umbilical cord is the mammalian tissue with one of the highest contents of Hyaluronic Acid (HA).

The umbilical cord forms the connection between the placenta and the fetus. It contains one vein and two (2) arteries surrounded by a myxomatous substance called Wharton's jelly, consisting of stem cells, high amounts of extracellular matrix components mainly collagen, hyaluronate and several sulphated proteoglycans. The large amount of hyaluronate make this tissue highly hydrated, whereas the abundant content of collagen makes it resistant to extension, bending, twisting and compression evoked by fetal movements and uterine contractions. Furthermore, the extracellular matrix of Wharton's jelly is an abundant reservoir of numerous cytokines, peptides and peptide growth.

The main components of umbilical cord tissue and Wharton's jelly are proteoglycans, macromolecules built of protein cores covalently attached to sulphated glycosaminoglycans. Proteoglycans perform numerous functions including: regulating the mechanical properties of tissues, regulation of collagen matrix organization, they participate in cell-cell and cell-extracellular matrix interactions, bind growth factors, enzymes, viruses, etc.

The above components serve as extracellular matrix components which are secreted molecules that constitute the cell microenvironment, composed of a dynamic and complex array of glycoproteins, collagens, glycosaminoglycans and proteoglycans. The extracellular matrix provides the bulk, shape and strength of many tissues. However, the extracellular matrix provides much more than just mechanical and structural support. ECM molecules can be flexible and extendable and mechanical tension can expose cryptic sites, which could further interact with growth factors, signaling molecules or their receptors.

Extracellular matrix (ECM) proteins play crucial and complex roles during cell surface receptor signaling. The ECM serves as a reservoir for growth factors and signaling molecules. ECM-bound growth factors are released and bind to their specific receptors. Many ECM proteins have binding sites for both cell adhesion and growth factors, allowing local concentration of the growth factors near to their cell surface receptors and cell adhesion sites.

Some of the growth factors and signaling molecules found in Wharton's jelly are involved in a wide variety of different cytokines and growth factors including involved in anti-cancer, wound healing, neuroprotection, liver protection, anti-inflammatory, etc. These specific factors include but are not limited to the factors defined below:

EGF—Epidermal Growth Factor: a mitogenic polypeptide produced by many cell types and made in large amounts by some tumors. It promotes growth and differentiation, is essential in embryogenesis, and is also important in wound healing. It has been found to be part of a family of compounds that includes also transforming growth factor.

PDGF—Platelet Derived Growth Factor: one of the numerous growth factors, or proteins that regulate cell growth and division. In particular, it plays a significant role in blood vessel formation (angiogenesis), the growth of blood vessels from already-existing blood vessel tissue.

aFGF—Acidic Fibroblast Growth Factor and bFGF—Basic Fibroblast Growth Factor: In normal tissue, basic fibroblast growth factor is present in basement membranes and in the subendothelial extracellular matrix of blood vessels. It stays membrane bound as long as there is no signal peptide. It has been hypothesized that, during both wound healing of normal tissues and tumor development, the action of heparan sulfate-degrading enzymes activates bFGF, thus mediating the formation of new blood vessels, a process known as angiogenesis. In addition, it is synthesized and secreted by human adipocytes and the concentration of bFGF correlates with the BMI in blood samples. In this study, bFGF was also shown to act on preosteoblasts—in the form of an increased proliferation—after binding to fibroblast growth factor receptor 1 and activating phosphoinositide 3-kinase. bFGF has been shown in preliminary animal studies to protect the heart from injury associated with a heart attack, reducing tissue death and promoting improved function after reperfusion.

IGF-1—Insulin Like Growth Factor 1: The primary action is mediated by binding to its specific receptor, the insulin-like growth factor 1 receptor (IGF1R), which is present on many cell types in many tissues. Binding to the IGF1R, a receptor tyrosine kinase, initiates intracellular signaling; IGF-1 is one of the most potent natural activators of the AKT signaling pathway, a stimulator of cell growth and proliferation, and a potent inhibitor of programmed cell death.

TGF-β—Transforming Growth Factor Beta: Involved in many cellular processes in both the adult organism and the developing embryo including cell growth, cell differentiation, apoptosis, cellular homeostasis and other cellular functions.

BDNF—Brain Derived Neurotropic Factor: BDNF acts on certain neurons of the central nervous system and the peripheral nervous system, helping to support the survival of existing neurons, and encourage the growth and differentiation of new neurons and synapses. In the brain, it is active in the hippocampus, cortex, and basal forebrain—areas vital to learning, memory, and higher thinking.

GDNF—Glial Derived Neurotrophic Factor GDNF: A protein that, in humans, is encoded by the GDNF gene. GDNF is a small protein that potently promotes the survival of many types of neurons. It signals through GFRα receptors, particularly GFRα1.

aG-CSF—Granulocyte Colony Stimulating Factor (G-CSF or GCSF), also known as colony-stimulating factor 3 (CSF 3), is a glycoprotein that stimulates the bone marrow to produce granulocytes and stem cells and release them into the bloodstream. Functionally, it is a cytokine and hormone, a type of colony-stimulating factor, and is produced by a number of different tissues. The pharmaceutical analogs of naturally occurring G-CSF are called filgrastim and lenograstim.

SDF-1—Stromal Cell Derived Factor 1 CXCL12: Plays an important role in angiogenesis by recruiting endothelial progenitor cells (EPCs) from the bone marrow through a CXCR4 dependent mechanism.

PDGF-AA—Platelet-Derived Growth Factor AA: PDGF-AA is one of the numerous growth factors, or proteins that regulate cell growth and division. In particular, it plays a significant role in blood vessel formation (angiogenesis), the growth of blood vessels from already-existing blood vessel tissue.

Angiopoietin-2: Angiopoietin is part of a family of vascular growth factors that play a role in embryonic and postnatal angiogenesis. Angiopoietin signaling most directly corresponds with angiogenesis, the process by which new arteries and veins form from preexisting blood vessels.

VEGF—Vascular Endothelial Growth Factor: Vascular endothelial growth factor (VEGF), originally known as vascular permeability factor (VPF), is a signal protein produced by cells that stimulates vasculogenesis and angiogenesis. It is part of the system that restores the oxygen supply to tissues when blood circulation is inadequate such as in hypoxic conditions.

CXCL-16—Chemokine Ligand 16 (CXCL) 16: One of the ELR-CXC chemokines, acts as a mediator of innate immunity by attracting CXC chemokine receptor (CXCR) 6-expressing cells, such as activated T cells and NKT cells.

NAP-2—Neutrophil-Activating Protein-2: Chemokine (C-X-C motif) ligand (CXCL7) is a small cytokine belonging to the CXC chemokine family. It is a protein that is released in large amounts from platelets following their activation. It stimulates various processes including mitogenesis, synthesis of extracellular matrix, glucose metabolism and synthesis of plasminogen activator.

(GITR) Glucocorticoid-induced Tumor Necrosis Factor Receptor: GITR is currently considered to be a co-stimulatory immune checkpoint molecule.

FGF-20 Fibroblast Growth Factor 20: FGF family members possess broad mitogenic and cell survival activities, and are involved in a variety of biological processes, including embryonic development cell growth, morphogenesis, tissue repair, tumor growth and invasion. This gene was shown to be expressed in normal brain, particularly the cerebellum. The rat homolog is preferentially expressed in the brain and able to enhance the survival of midbrain dopaminergic neurons in vitro.

IL-10—Interleukin-10: Interleukin 10 (IL-10), also known as human cytokine synthesis inhibitory factor (CSIF), is an anti-inflammatory cytokine. In humans, interleukin 10 is encoded by the IL10 gene.

IL-12—Interleukin-12: Interleukin 12 (IL-12) is an interleukin that is naturally produced by dendritic cells, macrophages, neutrophils, and human B-lymphoblastoid cells (NC-37) in response to antigenic stimulation.

IL-13—Interleukin-13: IL-13 has effects on immune cells that are similar to those of the closely related cytokine IL-4. However, IL-13 is suspected to be a more central mediator of the physiologic changes induced by allergic inflammation in many tissues. Although, IL-13 is associated primarily with the induction of airway disease, it also has anti-inflammatory properties. IL-13 induces a class of protein-degrading enzymes, known as matrix metalloproteinases (MMPs), in the airways. These enzymes are required to induce egression of effete parenchymal inflammatory cells into the airway lumen where they are then cleared.

IL-15—Interleukin-15: Interleukin 15 (IL-15) is a cytokine with structural similarity to IL-2. Like IL-2, IL-15 binds to and signals through a complex composed of IL-2/IL-15 receptor beta chain (CD122) and the common gamma chain (gamma-C, CD132). IL-15 is secreted by mononuclear phagocytes (and some other cells) following infection by virus(es). This cytokine induces cell proliferation of natural killer cells; cells of the innate immune system whose principal role is to kill virally infected cells.

IL-17A—Interleukin 17A: Signaling from IL-17 recruits monocytes and neutrophils to the site of inflammation in response to invasion by pathogens, similar to Interferon gamma. In promoting inflammation, IL-17 has been demonstrated to act synergistically with tumor necrosis factor and interleukin-1 This activity can also be redirected towards the host and result in various autoimmune disorders that involve chronic inflammation, such as the skin disorder psoriasis.

IL-1RA Interleukin—1 Receptor Agonist: IL-1RA is a member of the interleukin 1 cytokine family. IL1Ra is secreted by various types of cells including immune cells, epithelial cells, and adipocytes, and is a natural inhibitor of the pro-inflammatory effect of IL1β. This protein inhibits the activities of interleukin 1, alpha (IL1A) and interleukin 1, beta (IL1B), and modulates a variety of interleukin 1 related immune and inflammatory responses. This gene and five other closely related cytokine genes form a gene cluster spanning approximately 400 kb on chromosome 2. Four alternatively spliced transcript variants encoding distinct isoforms have been reported.

IL-9—Interleukin-9: This cytokine stimulates cell proliferation and prevents apoptosis. It functions through the interleukin-9 receptor (IL9R), which activates different signal transducer and activator (STAT) proteins and thus connects this cytokine to various biological processes.

IL-2—Interleukin-2: Interleukin-2 (IL-2) is an interleukin, a type of cytokine signaling molecule in the immune system. It is a protein that regulates the activities of white blood cells (leukocytes, often lymphocytes) that are responsible for immunity.

IL-3—Interleukin-3: Interleukin-3 (IL3) is a cytokine that regulates blood-cell production by controlling the production, differentiation and function of granulocytes and macrophages.

IL-4—Interleukin-4: The interleukin 4 (IL4) is a cytokine that induces differentiation of naive helper T cells (Th0 cells) to Th2 cells. Upon activation by IL-4, Th2 cells subsequently produce additional IL-4 in a positive feedback loop.

IL-5—Interleukin-5: Interleukin-5 is produced in lymphocytes, mast cells, eosinophils, and airway smooth muscle and epithelial cells, and is primarily responsible for the maturation and release of eosinophils in the bone marrow.

IL-6—Interleukin-6: Interleukin 6 (IL-6) is an interleukin that acts as both a pro-inflammatory cytokine and an anti-inflammatory myokine.

IL-7—Interleukin-7: Interleukin 7 (IL-7) is a protein that in humans is encoded by the IL7 gene. IL-7 is a hematopoietic growth factor secreted by stromal cells in the bone marrow and thymus. It is also produced by keratinocytes, dendritic cells, hepatocytes, neurons, and epithelial cells but is not produced by normal lymphocytes IL-8—Interleukin-8: Interleukin-8, also known as neutrophil chemotactic factor, has two primary functions. It induces chemotaxis in target cells, primarily neutrophils but also other granulocytes, causing them to migrate toward the site of infection. IL-8 also induces phagocytosis once they have arrived. IL-8 is also known to be a potent promoter of angiogenesis. In target cells, IL-8 induces a series of physiological responses required for migration and phagocytosis, such as increases in intracellular Ca2+, exocytosis (e.g. histamine release), and the respiratory burst.

MCP-1—Monocyte Chemotactic Protein 1: The chemokine (C-C motif) ligand 2 (CCL2) is also referred to as monocyte chemoattractant protein 1 (MCP1) and small inducible cytokine A2. CCL2 is a small cytokine that belongs to the CC chemokine family CCL2 recruits monocytes, memory T cells, and dendritic cells to the sites of inflammation produced by either tissue injury or infection.

In addition to the factors listed above, the MSCs found in Wharton's jelly have been reported to secrete a wide variety of different factors (tropism). These secreted trophic factors enhance angiogenesis, synaptogenesis and neurogenesis. These factors also have been shown to activate the PI3K-Akt pathway resulting in the inhibition of apoptosis, increased cell survival and a stimulation of angiogenesis; which is believed to be partly due to the release of angiogenic factors such as IL-6, VEGF, and monocyte chemoattractant protein (MCP)-1. These secreted factors also appear to increase the expression of local neurotransmitters, such as brain-derived neurotrophic factor (BDNF), neurotrophin-3 (NTF-3), which should enhance recovery as well as a variety of different factors that are involved in wound healing. These factors are released into the surrounding tissue.

Growth factors and cytokines exert their regulatory roles on various cells by their action on specific receptors. These growth factors may be present on the surface of the same cell that produces the growth factors (autocrine action). Alternatively, the growth factors may work on other target cells, which are not themselves the producer cell (paracrine action). In some cases, target cells may also occur in distant parts of the body, giving rise to a type of regulation analogous to the mode of action of polypeptide hormones (endocrine regulation).

Consequently, a further need exists to overcome the problems with the prior art as discussed above, and particularly for a more efficient and expeditious way of promoting healing and other therapeutic and regenerative effects in humans and other animals.

SUMMARY

This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

A method of preparation of a solution used for therapeutic and regenerative applications having a concentration of at least about 0.05 microgram of total protein extract is disclosed. The method comprises the steps of: collecting an umbilical cord; incubating the umbilical cord in a solution containing antibiotics for sterilization; washing the umbilical cord in a buffered salt solution; homogenizing the umbilical cord in the buffered salt solution so as to produce an aqueous solution comprising umbilical cord tissue proteins, cytokines, growth factors and RNA; applying an ultrasonic processer to the aqueous solution to sonicate and disrupt umbilical cord tissue, wherein the ultrasonic processor is applied at a power output of 300 W at a frequency of 20 kHz, wherein sonication occurs in 3 second cycles of 2 seconds on and 1 second off for a total duration of 5 minutes; placing the aqueous solution into a centrifuge to separate the aqueous solution into a soluble component and a non-soluble component (tissue and cellular debris); filtrating and discarding the non-soluble component of the aqueous solution from the centrifuge through a 0.2 micron filter; and measuring protein concentration of the soluble component to insure at least about 0.05 microgram of total protein extract.

To the accomplishment of the above and related objects, the claimed subject matter may be embodied in the form illustrated in the accompanying drawings, attention being called to the fact, however, that the drawings are illustrative only, and that changes may be made in the specific construction illustrated and described within the scope of the appended claims. The foregoing and other features and advantages of the claimed subject matter will be apparent from the following more particular description of the preferred embodiments, as illustrated in the accompanying drawings.

BRIEF DESCRIPTION OF THE DRAWINGS

The accompanying drawings, which are incorporated in and constitute part of this specification, illustrate embodiments of the claimed subject matter and together with the description, serve to explain the principles of the disclosed embodiments. The embodiments illustrated herein are presently preferred, it being understood, however, that the claimed subject matter is not limited to the precise arrangements and instrumentalities shown, wherein:

FIGS. 9A and 9B comprise photographs of experimental results of the use of the claimed therapeutic agent, according to one embodiment.

FIGS. 13A, 13B, 3C, and 3D comprise photographs of an experiment showing MSC growth in RPMI culture media, according to one embodiment, while FIG. 13E shows an MSC growth comparison graph.

DETAILED DESCRIPTION

Figure 1:
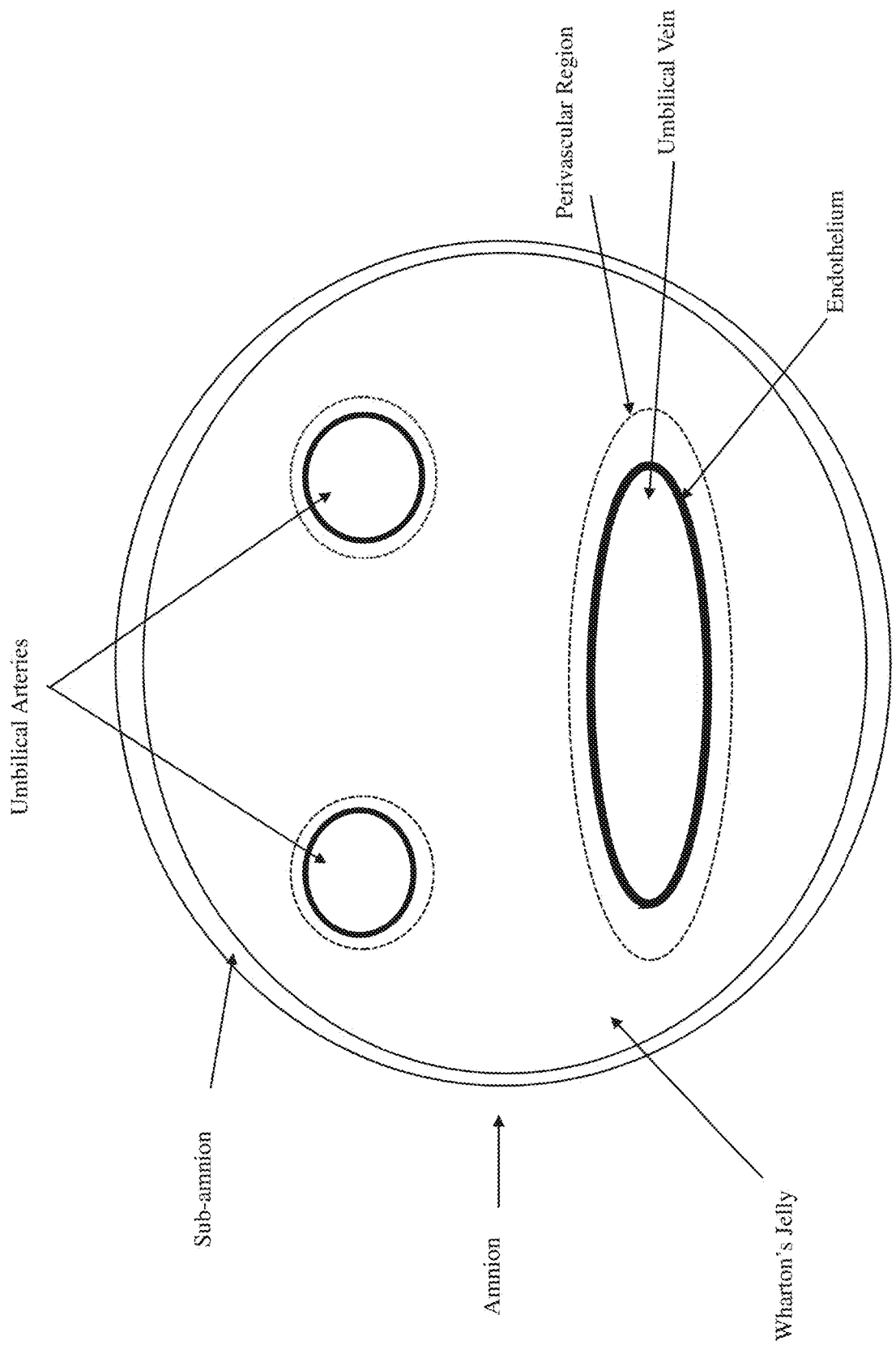
FIG. 1 is an illustration of a cross sectional view of an umbilical cord.
Figure 2A:
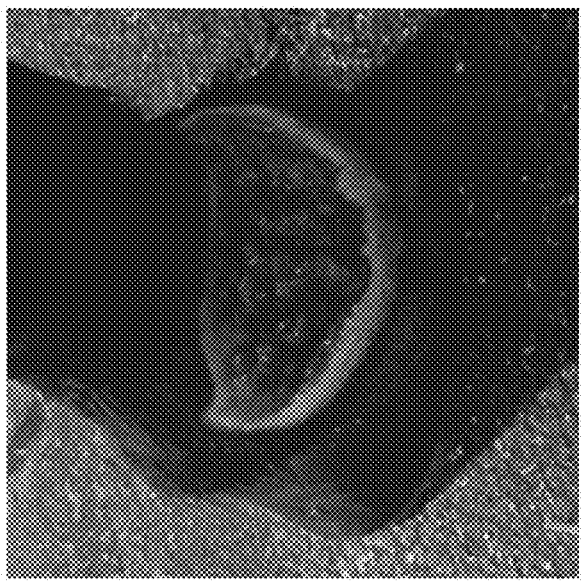
FIGS. 2A, 2B, 2C, and 2D comprise photographs of experimental results of the use of the claimed therapeutic agent, according to one embodiment.
Figure 2C:
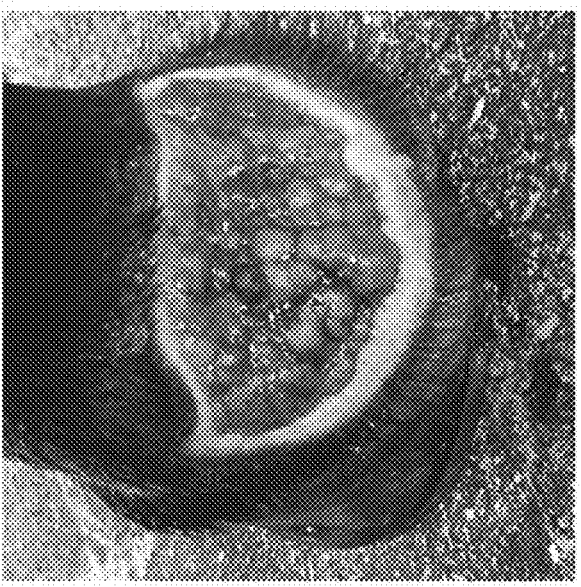
Figure 2B:
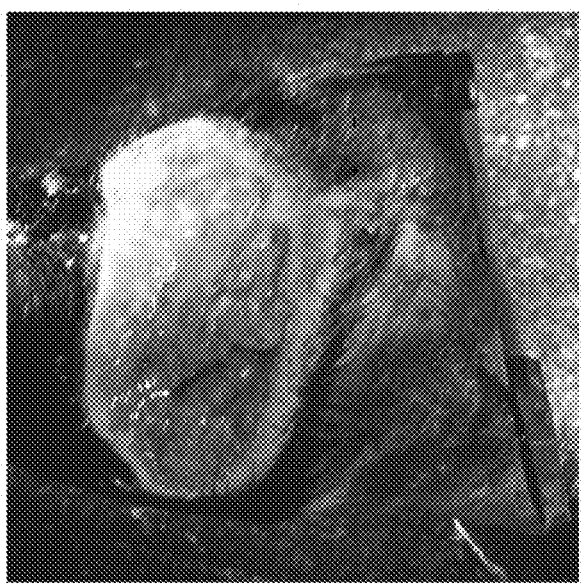
Figure 2D:
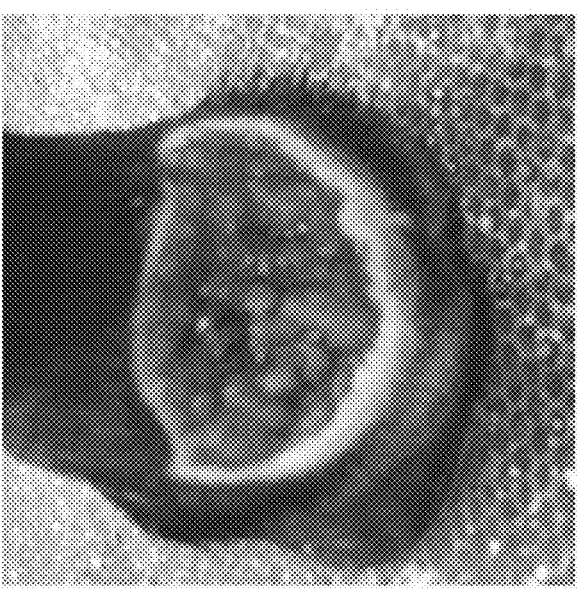

The disclosed embodiments are directed to a therapeutic and regenerative agent that promotes healing, reduces inflammation and treats various afflictions in animals, among other things. The disclosed embodiments improve over the prior art by providing a simple, inexpensive and quick method for producing said therapeutic agent for mass production and transport to individuals and consumers. The disclosed embodiments also improve over the prior art by providing an agent that can be used as cell-culture component/additive to promote the growth of desired cells.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The claimed process produces an acellular product, derived from umbilical cord tissue and Wharton's jelly that contains cytokines, growth factors, peptides, signaling molecules, proteins, RNA, exosomes and anti-inflammatory and regenerative molecules that can be used by itself or combined with a variety of different products including but not limited to; cream-base containing lipophilic agents and can be used to treat anti-inflammatory conditions in mammals (both human and veterinary applications), gel and agarose based products for the delivery of these factors to an external wound in mammals (both human and veterinary applications), can be aerosolized and used via a nebulizer to treat conditions of the lung, can be injected or administered systemically to treat a variety of conditions such as cardiac, neurologic, musculoskeletal, hepatic, and can be lyophilized or freeze-dried and reconstituted for long-term storage and use. The product can also be used as a serum replacement or cell culture additive to promote the growth of desired cells.

The claimed process discloses methods of generating a therapeutic and regenerative product from umbilical cord tissue and Wharton's jelly tissue. In one embodiment, the claimed process provides means of creating a therapeutic and regenerative product useful for the treatment of inflammatory conditions, wounds and degenerative conditions by producing an extract of umbilical cord tissue and Wharton's jelly. Many types of methods of creating a tissue extract may be used and chosen. In one embodiment, a method is selected from a group comprising; 1) sonication; 2) shearing by liquid flow; 3) exploding by pressure; 4) collision forces by impact of beads or paddles; 5) cryogenic grinding; 6) Mortar and Pestle; 7) Glass homogenizer; 8) Blender; 9) Rotor-Stator; 10) Potter-Elvehjem with PTFE Pestle; 11) French Press; 12) Amalgamators for Tubes; 13) High Throughput homogenizers; 14) Combination of the above methods, or any similar methods known in the art.

In some embodiments, the tissue extract is administered directly into the patient (human or animal). It is well known in the art that preparation of the extract before administration may be performed by various means, for example, said extract may be sterile-filtered or in some conditions concentrated or diluted. In one embodiment, the product can be directly administered by injection.

In other embodiments, the tissue extract is used as an active ingredient for the generation of a pharmaceutical formulation. This may comprise administration of the tissue extract therapeutic agent alone, or by way of known pharmaceutical formulations, including tablets, capsules, or elixirs for oral administration, suppositories for rectal administration, sterile solutions or suspensions for parenteral or intramuscular administration, liposomal or encapsulated formulations, formulations wherein the therapeutic agent is alone or conjugated to a delivery agent or vehicle, and the like. The solid form preparations intended to be converted to liquid form may contain, in addition to the active material, flavorings, colorants, stabilizers, buffers, artificial and natural sweeteners, dispersants, thickeners, solubilizing agents, and the like.

It is possible that therapeutic entities of the product will be administered with suitable carriers, excipients, and/or other agents that are incorporated into formulations to provide improved transfer, delivery, tolerance, and the like. A multitude of appropriate formulations can be found in the formulary known to all pharmaceutical chemists: Remington's Pharmaceutical Sciences (15.sup.th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin.TM.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the claimed subject matter, provided that the active ingredient in the formulation is not inactivated by the formulation and the formulation is physiologically compatible and tolerable with the route of administration. See also Powell et al. "Compendium of excipients for parenteral formulations" PDA J Pharm Sci Technol 52:238-311 (1998).

In one embodiment, one or more agents of the claimed process are nanoencapsulated into nanoparticles for delivery. The nanoencapsulation material may be biodegradable or non-degradable. The nanoencapsulation materials may be made of synthetic polymers, natural polymers, oligomers, or monomers. Synthetic polymers, oligomers, and monomers include those derived from polyalkyleneoxide precursor molecules, such as poly(ethylene oxide) (PEO), poly(ethylene glycol) (PEG) and copolymers with poly(propylene oxide) (PEG-co-PPO), poly (vinyl alcohol) (PVA), poly (vinylpyrrolidone) (PVP), poly(ethyloxazoline) (PEOX), polyaminoacids, and pseudopolyamino acids, and copolymers of these polymers. Copolymers may also be formed with other water-soluble polymers or water insoluble polymers, provided that the conjugate is water soluble. An example of a water-soluble conjugate is a block copolymer of polyethylene glycol and polypropylene oxide, commercially available as a Pluronic surfactant (BASF). Natural polymers, oligomers and monomers include proteins, such as fibrinogen, fibrin, gelatin, collagen, elastin, zein, and albumin, whether produced from natural or recombinant sources, and polysaccharides, such as agarose, alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives, and carrageen.

These polymers are merely exemplary of the types of nanoencapsulation materials that can be utilized and are not intended to represent all the nanoencapsulation materials within which entrapment is possible. In one embodiment, the therapeutic agent is administered in a topical formulation. Topical formulations are useful in the treatment of conditions associated with dermal diseases and joint disorders/joint pain.

For example, topical administration of the tissue extract may contain aqueous and non-aqueous gels, creams, multiple emulsions, microemulsions, liposomes, ointments, aqueous and non-aqueous solutions, lotions, aerosols, skin patches, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrrolidone). In one embodiment, the pharmaceutically acceptable carrier is a liposome or a transdermal enhancer.

Topical formulations of the product may include a dermatologically acceptable carrier, e.g., a substance that is capable of delivering the other components of the formulation to the skin with acceptable application or absorption of those components by the skin. The carrier will typically include a solvent to dissolve or disperse the therapeutic agent, and, optionally one or more excipients or other vehicle ingredients. Carriers useful in accordance with the topical formulations of the product may include, by way of non-limiting example, water, acetone, ethanol, ethylene glycol, propylene glycol, butane-1,3-diol, acrylates copolymers, isopropyl myristate, isopropyl palmitate, mineral oil, butter(s), aloe, talc, botanical oils, botanical juices, botanical extracts, botanical powders, other botanical derivatives, lanolin, urea, petroleum preparations, tar preparations, plant or animal fats, plant or animal oils, soaps, triglycerides, and keratin(s). Topical formulations of the product are prepared by mixing a compound with a topical carrier.

In other embodiments, moisturizers or humectants, sunscreens, fragrances, dyes, and/or thickening agents such as paraffin, jojoba, PABA, and waxes, surfactants, occlusives, hygroscopic agents, emulsifiers, emollients, lipid-free cleansers, antioxidants and lipophilic agents, may be added to the topical formulations. A topical formulation may be designed to be left on the skin and not washed shortly after application. Alternatively, the topical formulation may be designed to be rinsed off within a given amount of time after application.

In one aspect, potency of the tissue extract product may be quantified by assessing protein concentration. For quantification of anti-inflammatory and regenerative activity, the term "inflammation" will be understood to include any condition characterized by a localized or a systemic protective response, which may be elicited by physical trauma, infection, chronic diseases, such as those mentioned above, and/or chemical and/or physiological reactions to external stimuli (e.g., as part of an allergic response). Any such response may be manifested by heat, swelling, pain, redness, dilation of blood vessels and/or increased blood flow, invasion of the affected area by white blood cells, loss of function and/or any other symptoms known to be associated with inflammatory conditions. The term "inflammation" will thus also be understood to include any inflammatory disease, disorder or, any condition that has an inflammatory component associated with it, and/or any condition characterized by inflammation as a symptom, including, inter alia, acute, chronic, ulcerative, specific, allergic and necrotic inflammation, and other forms of inflammation. The term thus also includes inflammatory pain.

For the practice of the claimed subject matter supernatants generated by umbilical cord tissue & Wharton's jelly tissue extracts may be administered to the patient in an injection solution, which may be saline, lactated Ringers solution, mixtures of autologous plasma together with saline, or various concentrations of albumin with saline. Ideally pH of the injection solution is from about 6.4 to about 8.3, optimally 7.4. Excipients may be used to bring the solution to isotonicity such as, 4.5% mannitol or 0.9% sodium chloride, pH buffers, such as sodium phosphate. Other pharmaceutically acceptable agents can also be used to bring the solution to isotonicity, including, but not limited to, dextrose, boric acid, sodium tartrate, propylene glycol, polyols (such as mannitol and sorbitol) or other inorganic or organic solutes. Injection can be performed systemically, or more specifically, via routes of administration selected from; a) orally; b) intravenously; c) intramuscularly; d) intraperitoneally; e) intrathecally; f) alimentarily; g) intraspinally; h) intra-articularly; i) intra-joint; j) subcutaneously; k) buccally; l) vaginally; m) rectally; n) dermally; o) transdermally; p) ophthalmically; q) auricularly; r) mucosally; s) nasally; t) tracheally; u) bronchially; v) sublingually; w) intranodally; x) by any parenteral route; and y) via inhalation.

The manufacturing of the disclosed product may entail the collection of umbilical cord tissue. The umbilical cord is collected after the new offspring is delivered by clamping the cord proximal to the offspring and then by cutting the cord. The freshly cut umbilical cord is then placed into a sterile container containing buffered saline solution or similar buffered salt solution for transportation to the processing laboratory.

The umbilical cord is washed in salt buffer about three times and the vasculature may or may not be removed by micro-dissection and discarded. The dissected tissue is then washed about three more times in a salt buffer to remove any residual blood and homogenized into small fragments (less than 1 mm in size) using a tissue blender (or any other method known in the art), resulting in an aqueous solution. Homogenization is carried out at room temperature for 5 minutes at the highest setting. The umbilical cord may be homogenized in the buffered salt solution resulting in the production of an aqueous solution comprising umbilical cord tissue proteins, cytokines, growth factors and RNA.

The aqueous solution, including minced tissue and homogenized tissue, is then re-suspended in a salt buffer and subjected to sonication. This step uses blasts of ultrasonic sound waves to disrupt the cells and tissue to assist in the release of the different cytokines, peptides and peptide growth factors that will be the active components in the treatment of inflammation and regenerative medicine applications. Sonication occurs via a 300 W ultrasonic processing at 20 kHz with a total of 3 second pulse. 2 seconds of sonic pulse followed by 1 second of non-sonic pulse for a duration of 5 minutes. In summary, there will be 5 minutes of the 2 seconds on, 1 second off pulsing cycle. This results in the liberation of all the proteins necessary for a functional product. The resulting tissue fragments are 1 mm in size after sonication.

After sonication, the aqueous solution (including disrupted tissue and buffer) is transferred into centrifuge tubes and centrifuged at 5500-7000 rpm for 10 minutes to pellet all the tissue and cellular debris and to separate the aqueous solution into a soluble component and a non-soluble component. The supernatant containing all the cytokines, peptides, signaling molecules, and peptide growth factors is transferred into a new centrifuge tube and centrifuged again at 5500-7000 rpm for 10 minutes to complete the removal and sedimentation of the tissue and cellular debris. The supernatant is then passed through a 100 µM cell strainer to remove any left-over cellular debris, then it is passed through a 0.22 µM polypropylene syringe filter to sterile filter the supernatant, i.e., the process filtrates and discards the non-soluble component of the aqueous solution from the centrifuge through a 0.2 micron filter. Next, the protein concentration of the soluble component is measured to insure at least about 0.05 microgram of total protein extract up to about 2 micrograms of total protein extract. In one embodiment, the protein concentration of the soluble component is measured to insure 0.05 microgram of total protein extract. In another embodiment, the protein concentration of the soluble component is measured to insure 2 micrograms of total protein extract. The process may further comprise mixing the soluble component with liposomes, resulting in a mix, mixing the mix with cream as a vehicle for application to a mammal, so as to produce a mixed cream, and depositing the mixed cream in a container for transport to users.

The concentration of total protein extract is not recognized as a particular parameter that can be experimented with to increase or optimize the effectiveness of therapeutic and regenerative applications for treating or curing certain maladies. The particular concentration of total protein extract defined above (0.05 microgram and 2.0 micrograms) are significant because they are the result of over 18 months of laboratory and experimental testing of the claimed invention on mammals to find the correct protein extract concentrations, in order to achieve the desired effectiveness. Depending on certain conditions of a mammalian test subject, such as age, gender, height weight and general health, the use of improper concentrations of this product can result in negative side effects on the test subjects.

The total protein extract concentration for a therapeutically effective dose ranges from 0.001 µg/ml to 5 µg/ml and can be varied in order to adjust the effectiveness for specific disease states or treatments (i.e. lung treatment is substantially less concentrated than joint treatment). The therapeutically effective concentration range recited above is significant because it resulted in decreased negative side effects on the test subjects and increased the effectiveness of the therapeutic and regenerative applications in treating certain maladies—the purpose of the claimed invention.

With regarding to the sonication process, the method described herein includes applying an ultrasonic processer to the aqueous solution to sonicate and disrupt umbilical cord tissue, wherein the ultrasonic processor is applied at a power output of 300 W at a frequency of 20 kHz, wherein sonication occurs in 3 second cycles of 2 seconds on and 1 second off for a total duration of 5 minutes. The sonication profile described above (which include wattage output, frequency and cycle times) is not recognized as a particular parameter that can be experimented with to increase or optimize the effectiveness of producing a therapeutic dose of the claimed solution. The sonication profile described above is significant because it is the result of over 18 months of laboratory and experimental testing of the claimed invention to find the correct sonication profile, in order to achieve the desired therapeutic dose of the claimed solution. Different sonication profiles produce different results in the nature of the resulting solution and its ability to convey a therapeutic dose to the patient.

With regarding to the centrifuge process, the method described herein includes applying a centrifuge at 5500-7500 rpm. The centrifuge profile described above is not recognized as a particular parameter that can be experimented with to increase or optimize the effectiveness of producing a therapeutic dose of the claimed solution. The centrifuge profile described above is significant because it is the result of over 18 months of laboratory and experimental testing of the claimed invention to find the correct centrifuge profile, in order to achieve the desired therapeutic dose of the claimed solution.

Figure 3A:
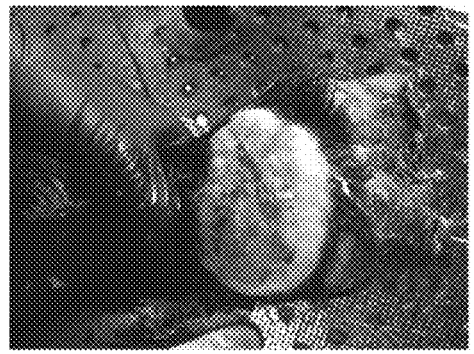
FIGS. 3A, 3B, 3C, and 3D comprise photographs of experimental results of the use of the claimed therapeutic agent, including dates and size measurements, according to one embodiment.
Figure 3B:
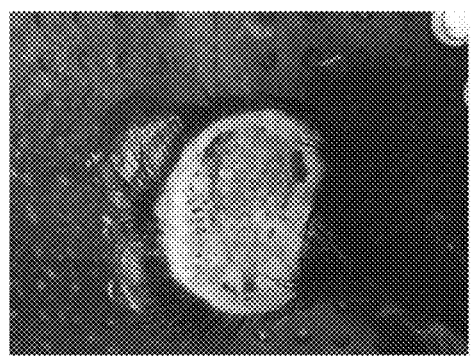
Figure 3C:
Figure 3D:
Figures 4A, 4B, 4C, 4D:
FIGS. 4A, 4B, 4C, and 4D comprise photographs of experimental results of the use of the claimed therapeutic agent, including dates and size measurements, according to one embodiment.
Figure 5B:
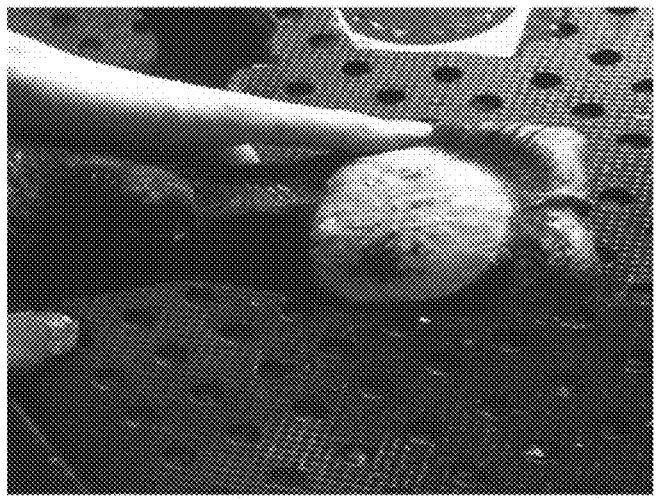
FIGS. 5A and 5B comprise photographs of experimental results of the use of the claimed therapeutic agent, including dates and size measurements, according to one embodiment.
Figure 5A:
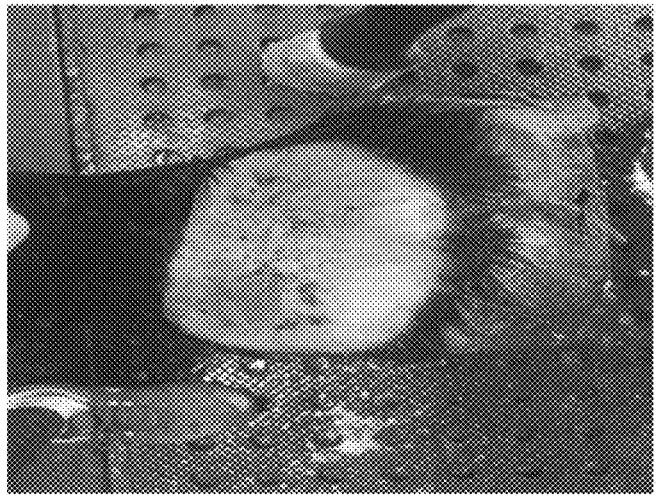

In a first example of experimental results, a three-year-old female horse suffered a severe burn during the removal of a wart on the back of the right front foot. The wound persisted for 2 months without any substantial healing. The picture shown in FIG. 2A was taken the first week after the burn occurred. Treatment with the UCT Wharton's jelly extract (i.e., the product produced by the claimed subject matter) began on May 9, 2016 with the extract being applied directly to the wound 3 times a week. The wound was wrapped, and measurements were taken. FIGS. 2A, 2B, 2C, and 2D show the progression of a wound over time. FIGS. 3A, 3B, 3C, 3D, 4A, 4B, 4C, 4D, 5A, and 5B show photographs of the same wound at various dates indicated, as well as the size of the wound, which clearly shows that the wound heals over time; due to the use of the product produced by the claimed subject matter. FIG. 3A, for example, shows a 5-9-2016 photograph of a wound sized 12 cm×4.5 cm×1.25 cm, while FIG. 3D shows a 5-22-2016 photograph of a wound sized 7 cm×3.75 cm×0.5 cm.

Figure 6C:
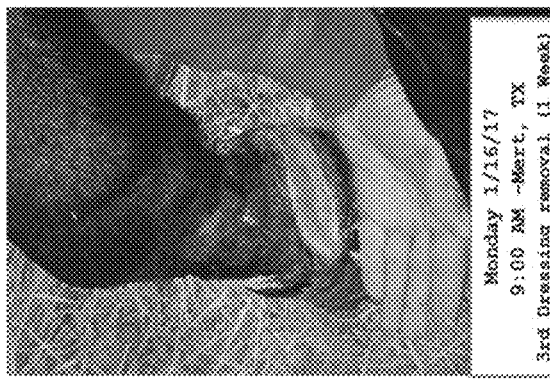
FIGS. 6A, 6B, 6C, and 6D comprise photographs of experimental results of the use of the claimed therapeutic agent, including dates, times, locations and descriptions, according to one embodiment.
Figure 6B:
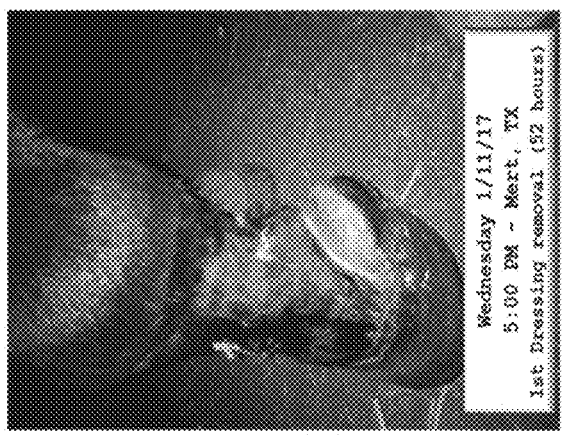
Figure 6A:
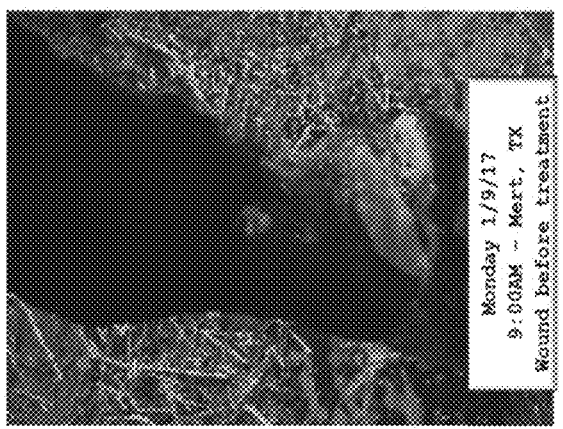
Figure 6D:

In a second example of experimental results, a horse that suffered a severe laceration to its hoof area. The product produced by the claimed subject matter was combined in a moisturizer like cream and applied to the wound 2× daily. FIGS. 6A, 6B, 6C, and 6D show photographs of the wound at various dates indicated, as well as the size of the wound, which clearly shows that the wound heals over time. FIG. 6A, for example, shows a 9 am 1-9-17 photograph taken in Mert, TX of a wound before treatment with the product produced by the claimed subject matter, while FIG. 6D shows a 4 pm 1-20-17 photograph taken in Mert, TX of said wound after treatment with the product produced by the claimed subject matter, clearly showing improvement.

Figure 7:
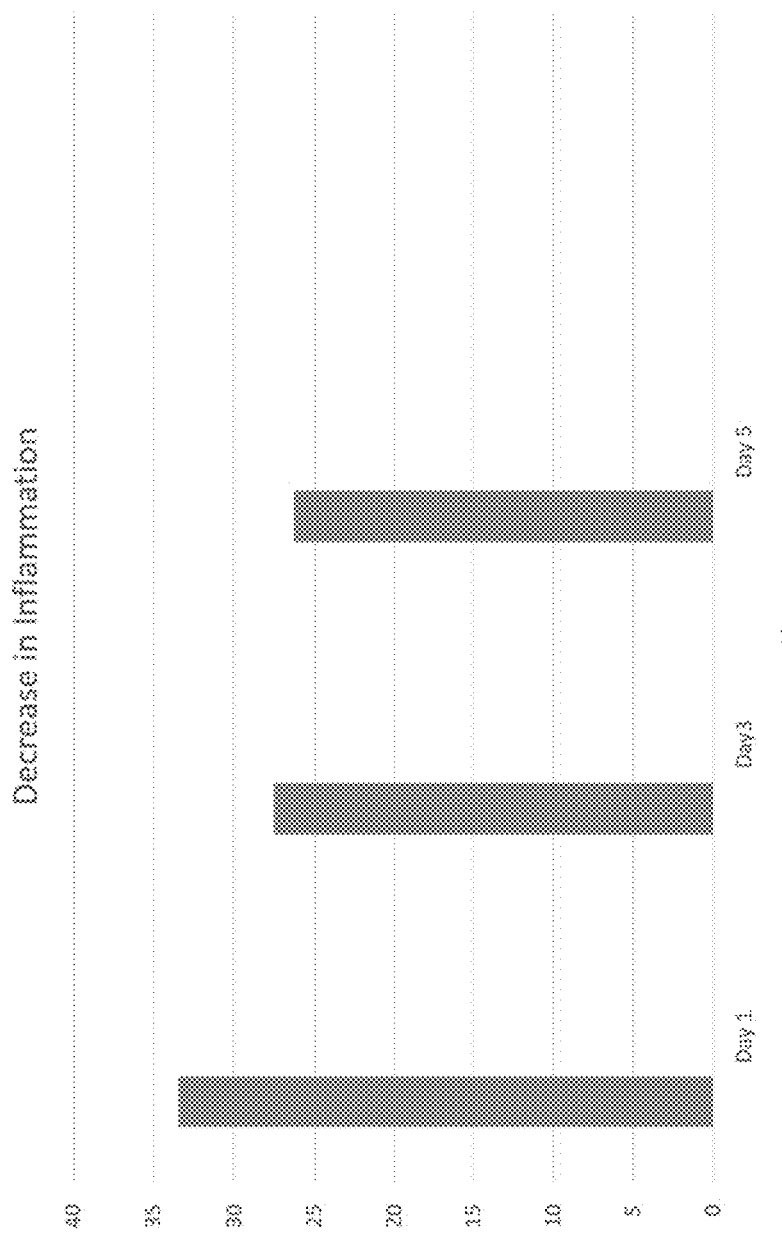
FIG. 7 is a chart showing inflammation measurements over time, for experimental results, according to one embodiment.

In a third example of experimental results, a 7-year-old male horse that broke his left fetlock at age 2. He has suffered from chronic suspensory branch lesions with scar tissue formation. The horse has been bandaged constantly and has had corrective shoeing performed to improve soundness with no improvements. The product produced by the claimed subject matter was applied to this horse 2× a day for 7 days with the following results demonstrating the decrease in inflammation in a very short period. FIG. 7 shows the decrease in inflammation due to the wound exhibited by the horse over time. FIG. 7 shows that the wound was about 32 cm in diameter on day 1 but shrank to about 26 cm in diameter at day 3 of the treatment.

Figure 8:
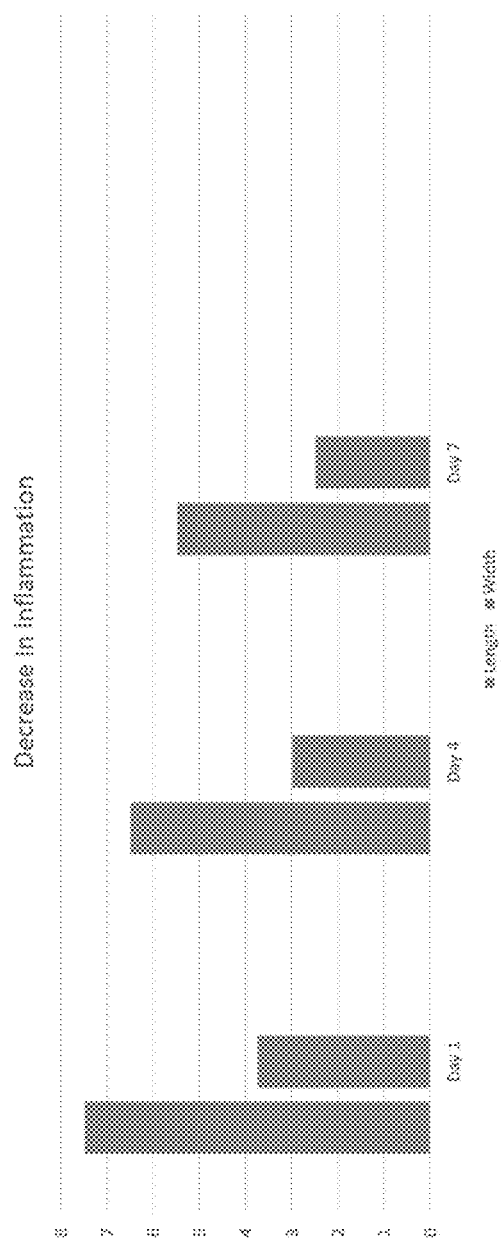
FIG. 8 is a chart showing inflammation measurements over time, for experimental results, according to one embodiment.
Figures 10A, 10B, 10C, 10D:
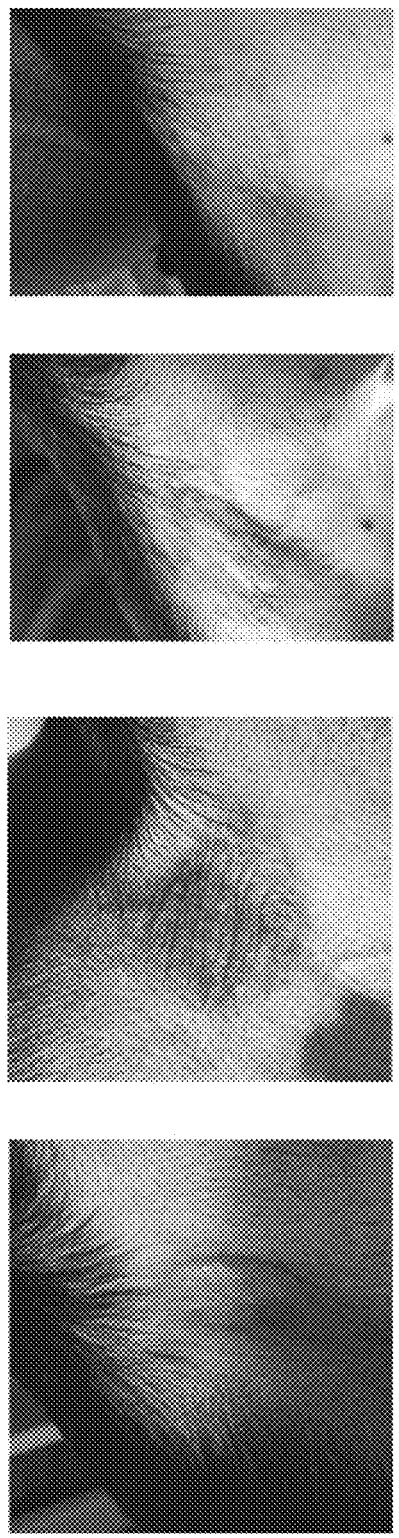
FIGS. 10A, 10B, 10C, and 10D comprise photographs of experimental results of the use of the claimed therapeutic agent, according to one embodiment.

In a fourth example of experimental results, a six-year-old male horse that suffered an injury where the splint bones popped. The injury did not heal resulting in physical calcification of the splint bone to the cannon bone causing inflammation and sensitivity to the suspensory ligament. The product produced by the claimed subject matter was applied 2× a day for 7 days. The injury occurred 4 months ago and was initially treated with surpass and poultice clay with no effect. This treatment was performed 4 months before the application of the extract. FIG. 8 shows the decrease in inflammation due to the wound exhibited by the horse over time. FIG. 8 shows that the wound was about 7.5 cm in length on day 1 but shrank to about 5.5 cm in length at day 7 of the treatment.

In a fifth example of experimental results, horse suffered a laceration above its eye that required sutures. The product produced by the claimed subject matter was administered after the sutures were performed 2 times a day. The results of wound closure were from 3 days application of the claimed product. FIG. 9A shows the original wound, while FIG. 9B shows the fully healed wound.

In a sixth example of experimental results, an 8-month-old puppy exhibited an ulcer on its pectoral area that turned out to be a Staph aureus infection (confirmed by independent testing lab and an independent physician). After four days of treatment with the product produced by the claimed subject matter and a wound cream, there was total clearance of the Staph infection. FIGS. 10A, 10B, 10C, and 10D show photographs of the wound at different dates, which clearly shows that the wound heals over time. Anti-microbial activity could be attributed to 2 possible mechanisms: the first is that the umbilical extract contains antimicrobial peptides that play a direct role in the antimicrobial activity, or secondly, there are numerous cytokines and immune signaling molecules present in the claimed produce that there is a massive influx of immune cells into the location where the cream has been administered.

Figure 11:
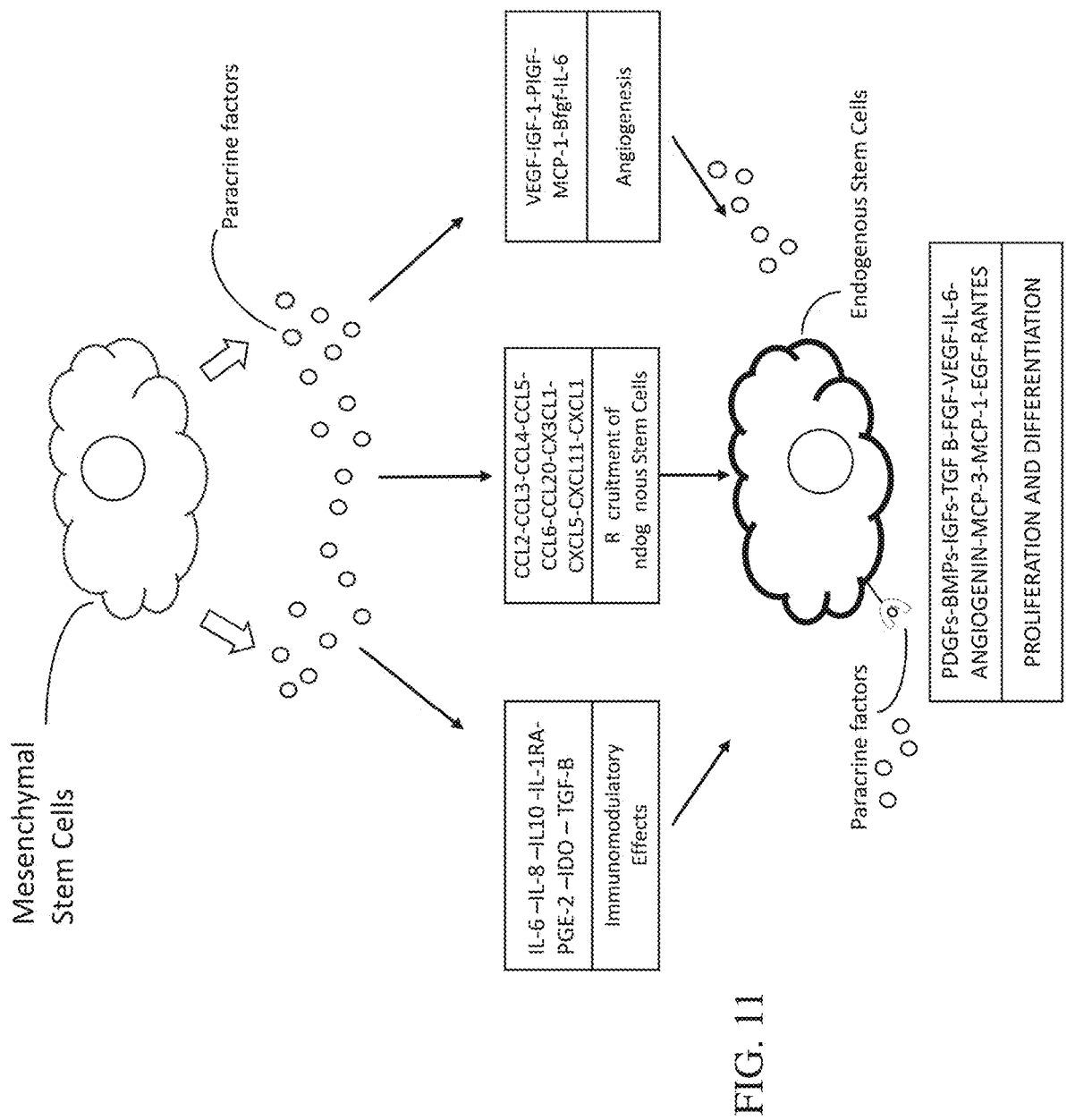
FIG. 11 is an illustration of the paracrine effects of stem cells.
Figure 12A:
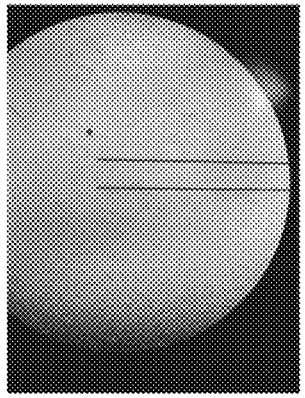
FIGS. 12A, 12B, 12C, and 12D comprise photographs of an experiment showing MSC growth in RPMI culture media, according to one embodiment.
Figure 12D:
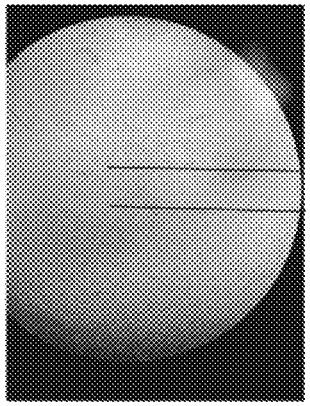
Figure 12B:
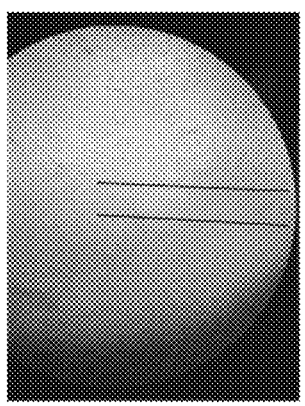
Figure 12E:
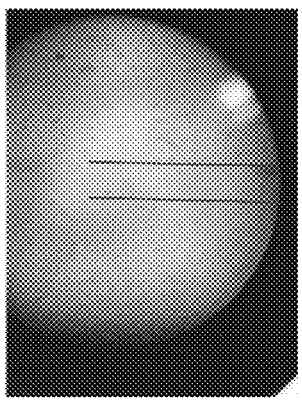
Figure 12C:
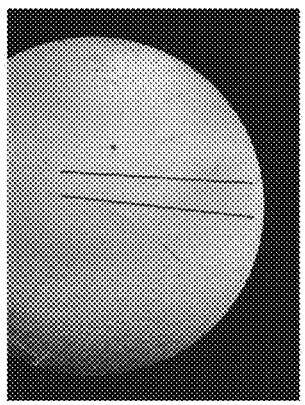
Figure 12F:
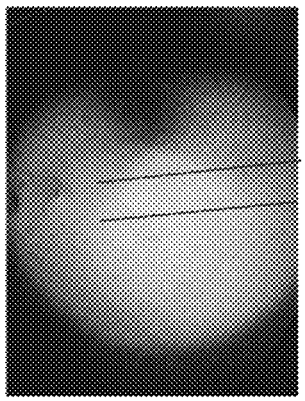

One possible mechanism of action of the product produced by the claimed subject matter is that it recruits endogenous stem cells to the location that it is applied to or injected into. See FIG. 11 for a description of said mechanism, which includes the paracrine factors, and shows how the immunomodulatory effects, angiogenesis and recruitment of endogenous stem cells are processed for proliferation and differentiation. In an attempt to demonstrate this experimentally, MSC migration assays were performed. MSCs were seeded 24 into culture containing a filter paper soaked in product produced by the claimed subject matter and a control was performed with the filter paper soaked in standard RPMI culture media. The cells in the product produced by the claimed subject matter media can be clearly seen migrating and filling in the area where the filter paper was at the 24 hour time point (paper removed to show the cells) and with the control media, RPMI, no cell migration can be seen. See FIGS. 12 and 13. FIG. 12A shows culture media with the claimed subject matter at an initial time, while FIG. 12B shows the media after 3 hours, FIG. 12C shows the media after 6 hours, FIG. 13A shows the media after 9 hours, and FIG. 13B shows the media after 24 hours. FIG. 12D shows the control RPMI culture media at an initial time, while FIG. 12E shows the RPMI culture after 3 hours, FIG. 12F shows the RPMI culture after 6 hours, FIG. 13C shows the RPMI culture after 9 hours, and picture FIG. 13D shows the RPMI culture after 24 hours. Additionally it was observed that MSCs proliferation was always greater in media supplemented with the product produced by the claimed subject matter versus media supplemented with FBS. Thus, the product produced by the claimed subject matter can be used as cell culture.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A method of preparation of a solution used for therapeutic and regenerative applications having a concentration of at least 0.05 micrograms of total protein extract, the method comprising the steps of:
   a) collecting an umbilical cord;
   b) incubating the umbilical cord in a solution containing antibiotics for sterilization at a temperature not exceeding 40 degrees Centigrade;
   c) washing the umbilical cord in a first buffered salt solution;
   d) homogenizing the umbilical cord in a second buffered salt solution so as to produce an aqueous solution comprising umbilical cord tissue proteins, cytokines, growth factors, and RNA, wherein said proteins comprise Brain Derived Neurotropic Factor (BDNF), Glial Derived Neurotrophic Factor (GDNF), Stromal Cell Derived Factor 1 (SDF-1), Angiopoietin-2, Chemokine Ligand 16 (CXCL-16), Neutrophil-Activating Protein-2 (Nap-2), Glucocorticoid-induced Tumor Necrosis Factor Receptor (GITR), and Fibroblast Growth Factor 20 (FGF-20);
   e) applying an ultrasonic processer to the aqueous solution to sonicate and disrupt umbilical cord tissue, wherein the ultrasonic processor is applied at a power output of 300 W at a frequency of 20 kHz, wherein sonication occurs in 3 second cycles of 2 seconds on and 1 second off for a total duration of 5 minutes;
   f) placing the aqueous solution into a centrifuge at about 5,500-7,500 rpm to separate the aqueous solution into a soluble component and a non-soluble component;

g) filtrating the non-soluble component of the aqueous solution from the centrifuge through a 0.2 micron filter and discarding the non-soluble component that was filtered; and h) measuring protein concentration of the soluble component to ensure at least 0.05 microgram of total protein extract.

2. The method of claim 1, wherein the solution that is used for therapeutic and regenerative applications has a therapeutically effective dose ranging from 0.001 µg/ml to 5 µg/ml.

3. The method of claim 2, wherein the step of collecting the umbilical cord further comprises collecting an umbilical cord from a mammal at the time of birth of an offspring of the mammal.

4. The method of claim 3, wherein the step of homogenizing the umbilical cord further comprises breaking up the umbilical cord in the second buffered salt solution using a blender for 5 minutes at room temperature so as to produce an aqueous solution, including minced tissue less than 1 mm in size.

5. The method of claim 4, wherein the step of placing the aqueous solution into a centrifuge further comprises placing the aqueous solution into a centrifuge at about 6,000 rpm.

6. The method of claim 5, wherein the soluble component is combined with a pharmaceutically acceptable carrier, resulting in a mixture.

7. A method of preparation of a solution for topical application having a concentration of at least 2 micrograms of total protein extract, the method comprising the steps of:

a) collecting a mammalian umbilical cord;

b) incubating the umbilical cord in a solution containing antibiotics for sterilization at a temperature not exceeding 40 degrees Centigrade;

c) washing the umbilical cord in a first buffered salt solution;

d) homogenizing the umbilical cord for 5 minutes in a second buffered salt solution so as to produce an aqueous solution comprising umbilical cord tissue proteins, cytokines, growth factors, and RNA, wherein said proteins comprise Brain Derived Neurotropic Factor (BDNF), Glial Derived Neurotrophic Factor (GDNF), Stromal Cell Derived Factor 1 (SDF-1), Angiopoietin-2, Chemokine Ligand 16 (CXCL-16), Neutrophil-Activating Protein-2 (Nap-2), Glucocorticoid-induced Tumor Necrosis Factor Receptor (GITR), and Fibroblast Growth Factor 20 (FGF-20);

e) applying an ultrasonic processer to the aqueous solution to sonicate and disrupt the umbilical cord tissue, wherein the ultrasonic processor is applied at a power output of 300 W at a frequency of 20 kHz, wherein sonication occurs in 3 second cycles of 2 seconds on and 1 second off for a total duration of 5 minutes;

f) placing the aqueous solution into a centrifuge at 5,500-7,500 rpm to separate the aqueous solution into a soluble component and a non-soluble component;

g) filtrating the non-soluble component of the aqueous solution from the centrifuge through a 0.2 micron filter and discarding the non-soluble component that was filtered; and h) measuring protein concentration of the soluble component to ensure at least 2 micrograms of total protein extract.

8. The method of claim 7, wherein the soluble component of the aqueous solution has a concentration of at least 2 micrograms of total protein extract, resulting in a therapeutically effective dose.

9. The method of claim 8, wherein the step of collecting the umbilical cord further comprises collecting an umbilical cord from a mammal at the time of birth of an offspring of the mammal.

10. The method of claim 9, wherein the step of homogenizing the umbilical cord further comprises breaking up the umbilical cord in the second buffered salt solution using a blender for 5 minutes at room temperature so as to produce an aqueous solution including minced tissue less than 1 mm in size.

11. The method of claim 10, wherein the step of measuring the protein concentration of the soluble component further comprises measuring additional characteristics of the soluble component.

12. The method of claim 11, further comprising mixing the soluble component with liposomes, resulting in a mix.

13. The method of claim 12, further comprising mixing the mix with cream as a vehicle for application to a mammal, so as to produce a mixed cream.

* * * * *